(12) United States Patent
Madsen

(10) Patent No.: US 12,285,758 B2
(45) Date of Patent: Apr. 29, 2025

(54) IN VITRO DIAGNOSTIC DEVICE WITH INTEGRATED PLASMA SEPARATOR

(71) Applicant: Fenwal, Inc., Lake Zurich, IL (US)

(72) Inventor: James Madsen, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 490 days.

(21) Appl. No.: 17/500,251

(22) Filed: Oct. 13, 2021

(65) Prior Publication Data
US 2022/0111383 A1  Apr. 14, 2022

Related U.S. Application Data

(60) Provisional application No. 63/091,405, filed on Oct. 14, 2020.

(51) Int. Cl.
*B01L 3/00* (2006.01)
*G01N 1/40* (2006.01)

(52) U.S. Cl.
CPC ...... *B01L 3/502753* (2013.01); *G01N 1/4005* (2013.01); *B01L 2200/0631* (2013.01); *B01L 2200/10* (2013.01); *B01L 2300/0681* (2013.01); *B01L 2300/0858* (2013.01); *B01L 2300/0864* (2013.01); *B01L 2300/087* (2013.01); *B01L 2400/0481* (2013.01)

(58) Field of Classification Search
None
See application file for complete search history.

(56) References Cited

U.S. PATENT DOCUMENTS

| | | | | |
|---|---|---|---|---|
| 6,471,855 | B1 * | 10/2002 | Odak | A61M 1/36225 |
| | | | | 210/512.1 |
| 2007/0197922 | A1 * | 8/2007 | Bradley | G01L 15/00 |
| | | | | 600/488 |
| 2013/0150225 | A1 * | 6/2013 | Katz | G01L 9/14 |
| | | | | 73/705 |
| 2013/0334139 | A1 | 12/2013 | Blickhan et al. | |
| 2016/0074565 | A1 | 3/2016 | Giordano et al. | |

FOREIGN PATENT DOCUMENTS

WO  2002056992  7/2002

OTHER PUBLICATIONS

European Patent Office, "Extended European Search Report", issued in connection with European patent application No. 21202311.3 on Jan. 5, 2022, 10 pages.

* cited by examiner

*Primary Examiner* — Lore R Jarrett
(74) *Attorney, Agent, or Firm* — Cook Alex Ltd.

(57) ABSTRACT

A lab-on-a-chip cartridge includes a housing defining four separate chambers. A fluid (such as whole blood) flows through one of the chambers and into another one of the chambers, which includes a filter membrane. The filter membrane is rotated to separate a first fluid component (such as plasma) from a second fluid component (such as red blood cells), with the first fluid component passing through the filter membrane and the second fluid component not passing through the filter membrane. The separated first and second fluid components each flow into a different one of the remaining chambers, with the first fluid component contacting a lab-on-a-chip device for analyzing the first fluid component.

20 Claims, 16 Drawing Sheets

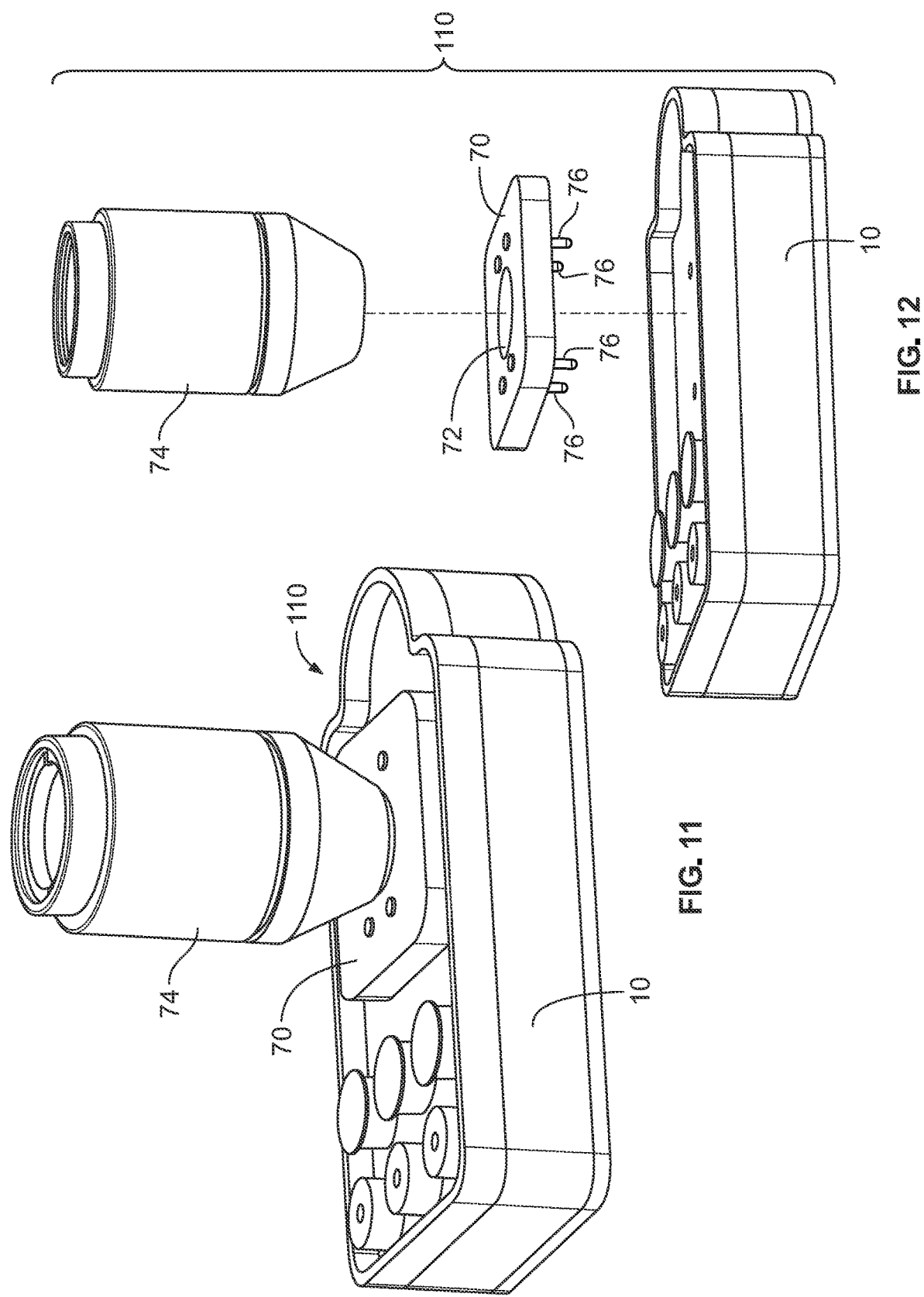

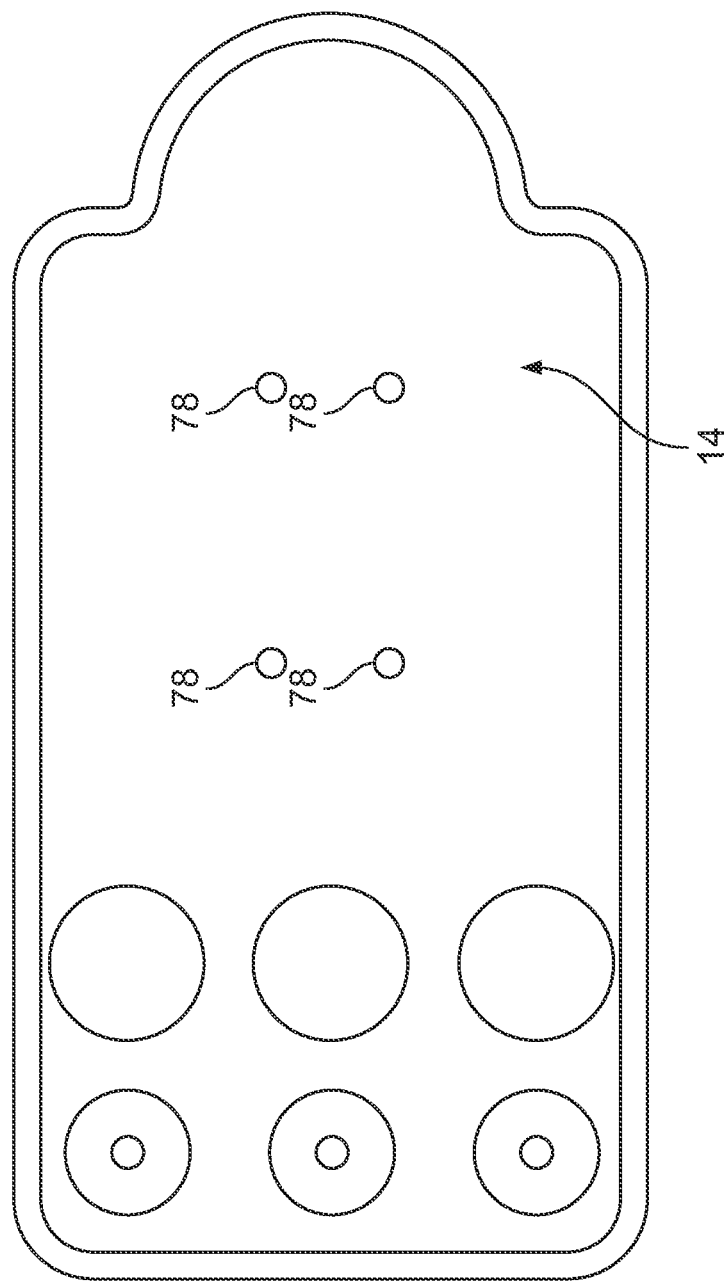

IN VITRO DIAGNOSTIC DEVICE WITH INTEGRATED PLASMA SEPARATOR

CROSS-REFERENCE TO RELATED APPLICATIONS

This application claims the benefit and priority of U.S. Provisional Patent Application Ser. No. 63/091,405, filed Oct. 14, 2020, the contents of which are incorporated by reference herein.

BACKGROUND

In vitro diagnostics (IVD) are tests done on samples, such as blood or tissue, taken from a human subject. IVD can detect diseases or other conditions, and can be used to monitor a person's overall health and to help cure, treat or prevent diseases. IVD can also be used in precision medicine to identify patients who are likely to benefit from specific treatments or therapies.

Lab-on-a-chip devices (LOCs) are commonly used in IVD. An LOC is a device that integrates one or several laboratory functions on a single integrated circuit (or chip) to achieve automation and high-throughput screening. LOCs can handle extremely small fluid volumes, down to less than pico-liters.

Lab-on-a-chip technology may soon become an important part of efforts to improve global health, particularly through the development of point-of-care ("POC") testing devices. In countries with few healthcare resources, infectious diseases that would be treatable in a developed nation are often deadly. In some cases, poor healthcare clinics have the drugs to treat a certain illness, but lack the diagnostic tools to identify patients who should receive the drugs. Many researchers believe that LOC technology may be the key to powerful new diagnostic instruments. The goal of these researchers is to create microfluidic chips that will allow healthcare providers in poorly equipped clinics to perform diagnostic tests such as immunoassays and nucleic acid assays with no laboratory support.

LOCs may provide advantages, which are specific to their application. Typical advantages are: low fluid volumes consumption (less waste, lower reagents costs and less required sample volumes for diagnostics); faster analysis and response times due to short diffusion distances, fast heating, high surface to volume ratios, small heat capacities; better process control because of a faster response of the system (e.g. thermal control for exothermic chemical reactions); compactness of the systems due to integration of much functionality and small volumes; massive parallelization due to compactness, which allows high-throughput analysis; lower fabrication costs, allowing cost-effective disposable chips, fabricated in mass production; and safer platform for chemical, radioactive or biological studies because of integration of functionality, smaller fluid volumes and stored energies.

Within the field of IVD, small volumes of whole blood are collected from patients for analysis of circulating biomarkers. The analysis of plasma biomarkers can diagnose many diseases, such as cancer, Alzheimer's disease, or sepsis. Typically, plasma is separated from whole blood before analysis to prevent contamination of the biomarkers by the presence of leukocytes, erythrocytes and hemolysis, which could increase test variability and reduce test accuracy.

The current state of the art for acquiring plasma for LOC devices consists of either using a traditional bench-top centrifuge or using plasma separation filters. When using a bench-top centrifuge, the whole blood sample is placed into the centrifuge and spun down, allowing for plasma extraction. Although centrifugation is an efficient method of plasma separation, it takes time and requires a two-step process wherein plasma is first extracted in a stand-alone centrifuge and then subsequently placed into a LOC device for biomarker analysis. This two-step process does not lend itself to point-of-care devices.

The second standard method of using a plasma separation filter functions by capillary action to draw small volumes (about 50 µl) of whole blood through a tortuous path filter to extract plasma. Capillary action is the driving force for these filters, and they stop extracting plasma upon becoming completely wetted out. While filters work adequately for very small plasma volumes, they are unable to process larger volumes which may be required for analysis of low concentration biomarkers. Using a plasma separation filter is also a two-step process, wherein plasma is separated from the whole blood using a filter and then subsequently placed into a LOC device for biomarker analysis. Again, this two-step process does not lend itself to point-of-care devices.

By way of the present disclosure, an integrated LOC device is provided that extracts plasma from a whole blood sample that is placed directly into a point-of-care device and analyzed.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately, or the claiming of such aspects separately or in different combinations as set forth in the claims appended hereto.

In a first aspect, a lab-on-a-chip cartridge is provided that comprises a housing having a plurality of side wall members defining first, second, third and fourth separate chambers on the interior of the cartridge. Each of the first, second and third chambers has a pump interface associated therewith, and at least the first chamber has a port through which a fluid may be introduced into the first chamber. A filter membrane is rotatably mounted in the fourth chamber so as to define a gap between an outer surface of the membrane and an inner surface of the side wall member defining the fourth chamber. A first passageway is provided in the side wall member between the first chamber and the gap in the fourth chamber for flowing a fluid from the first chamber into the gap between the filter membrane and the inner surface of the fourth chamber. A first flow path is provided that extends between the fourth chamber and the second chamber to permit fluid flow between the inner surface of the membrane and the second chamber, with a lab-on-a chip device being positioned within the first flow path for contact with fluid flowing from the fourth chamber into the second chamber. A second flow path extends between the fourth chamber and the third chamber to permit fluid flow between the gap in the fourth chamber and the third chamber. An interface in an exterior surface of the fourth chamber is provided for coupling a drive device with the membrane for rotating the membrane within the fourth chamber.

In a second aspect, the housing of the lab-on-a-chip further comprises a top plate, a bottom plate, and an intermediate plate defining the side wall members positioned between the top and bottom plates, the first flow path, second flow path, pump interfaces, port, and drive device interface being contained within one of the top and bottom plates.

In a third aspect, the pump interfaces comprise a recessed well sealed with a flexible diaphragm.

In a fourth aspect, each of the second and third chambers includes a port through which a fluid may be extracted.

In a fifth aspect any or all of the injection and extraction ports may have an adhesive seal associated therewith for providing access to or sealing the port.

BRIEF DESCRIPTION OF THE DRAWINGS

FIG. 11 is a perspective view of the lab-on-a-chip cartridge of FIG. 1 having an interface associated with the top plate that provides for, among other things, viewing of the chip in combination with a microscope objective lens.

FIG. 12 is an exploded perspective view of the lab-on-a-chip cartridge, interface, and lens of FIG. 11.

FIG. 14 is a top view of the top plate of the lab-on-a-chip cartridge of FIG. 13 with the interface removed.

DETAILED DESCRIPTION

Figure 1:
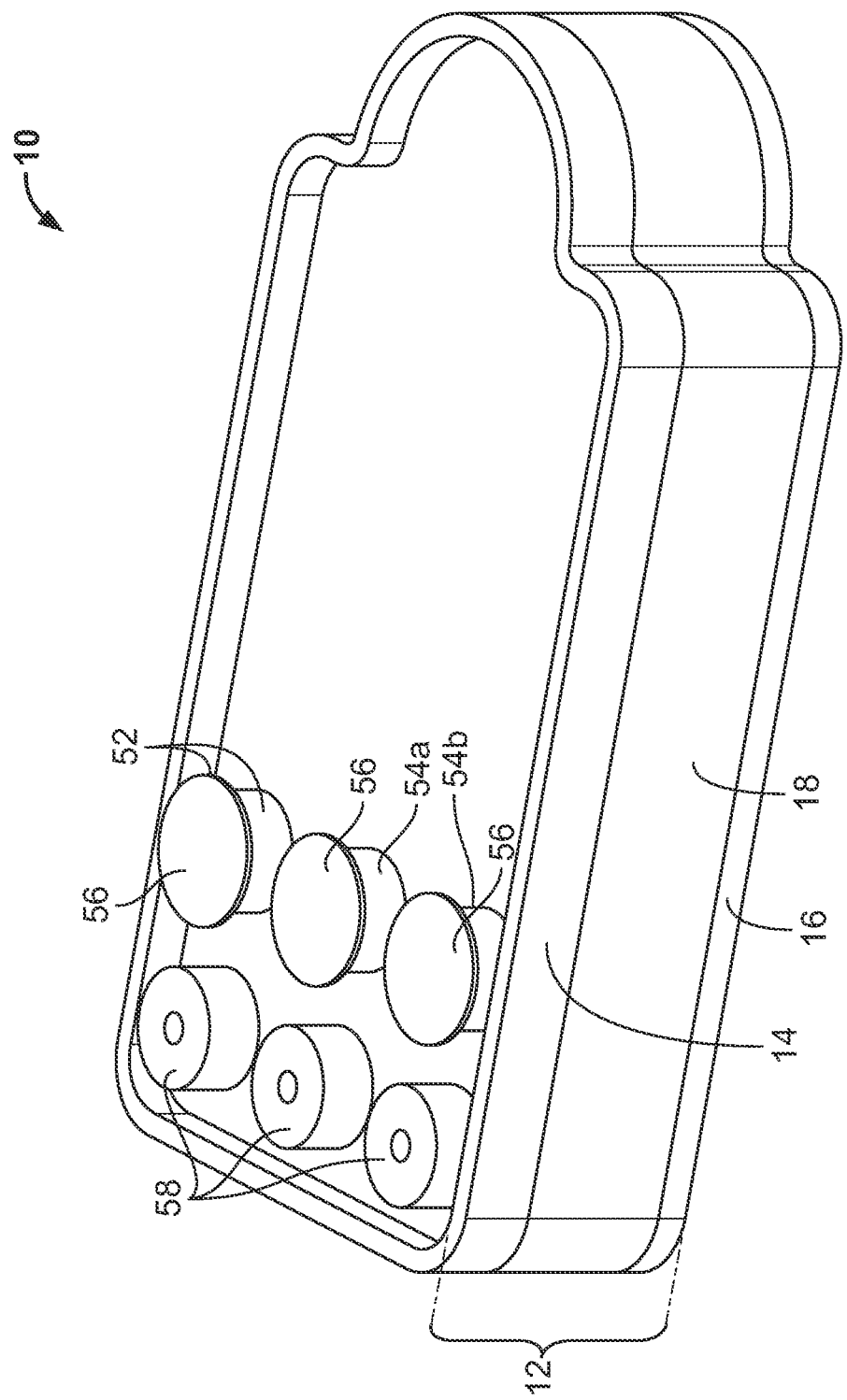
FIG. 1 is a perspective view of a lab-on-a-chip cartridge having an integral spinning membrane separator according to the present disclosure, with interior structures shaded to show detail.
Figure 2:
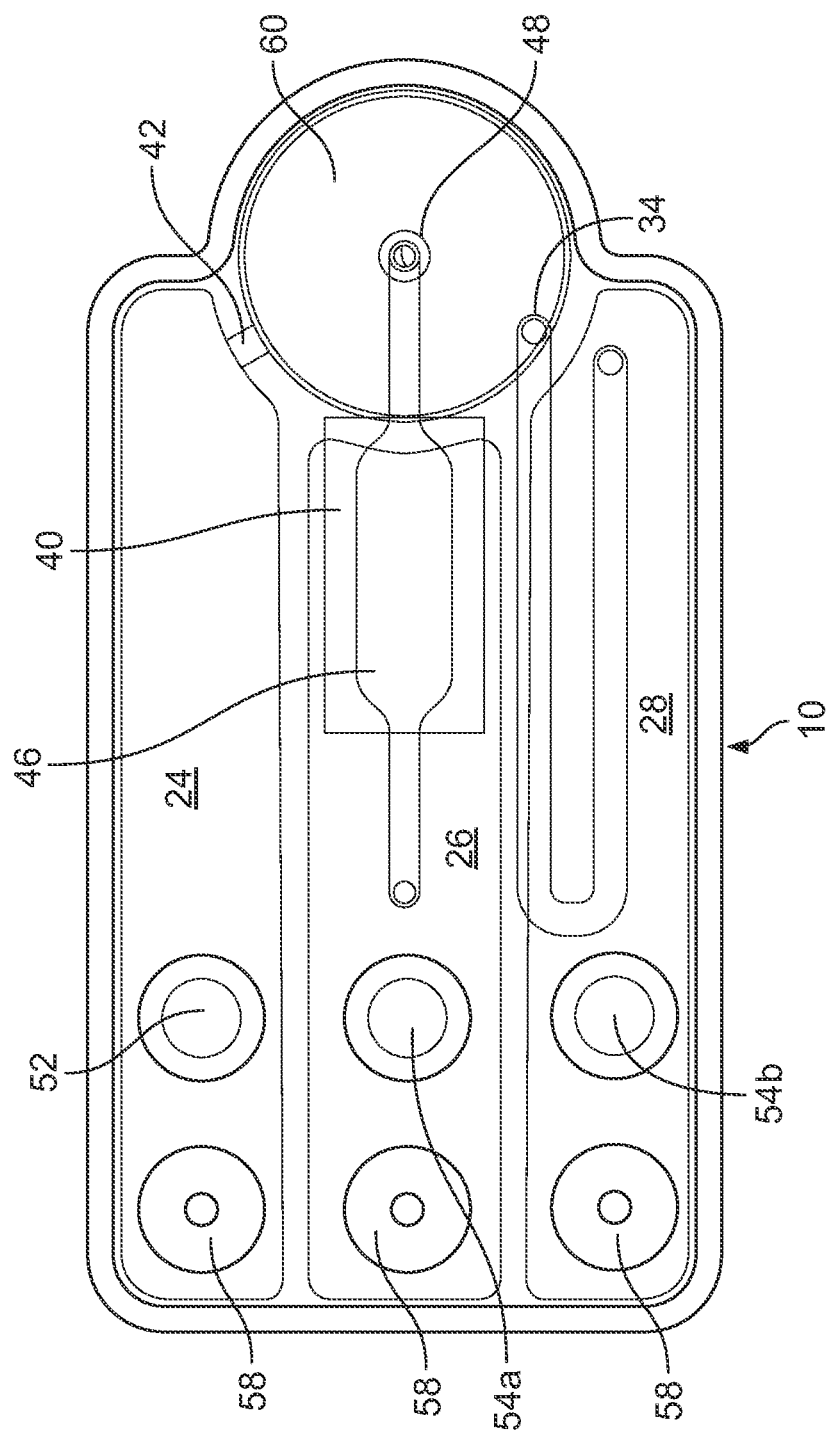
FIG. 2 is a top view of the lab-on-a-chip cartridge of FIG. 1.
Figure 3:
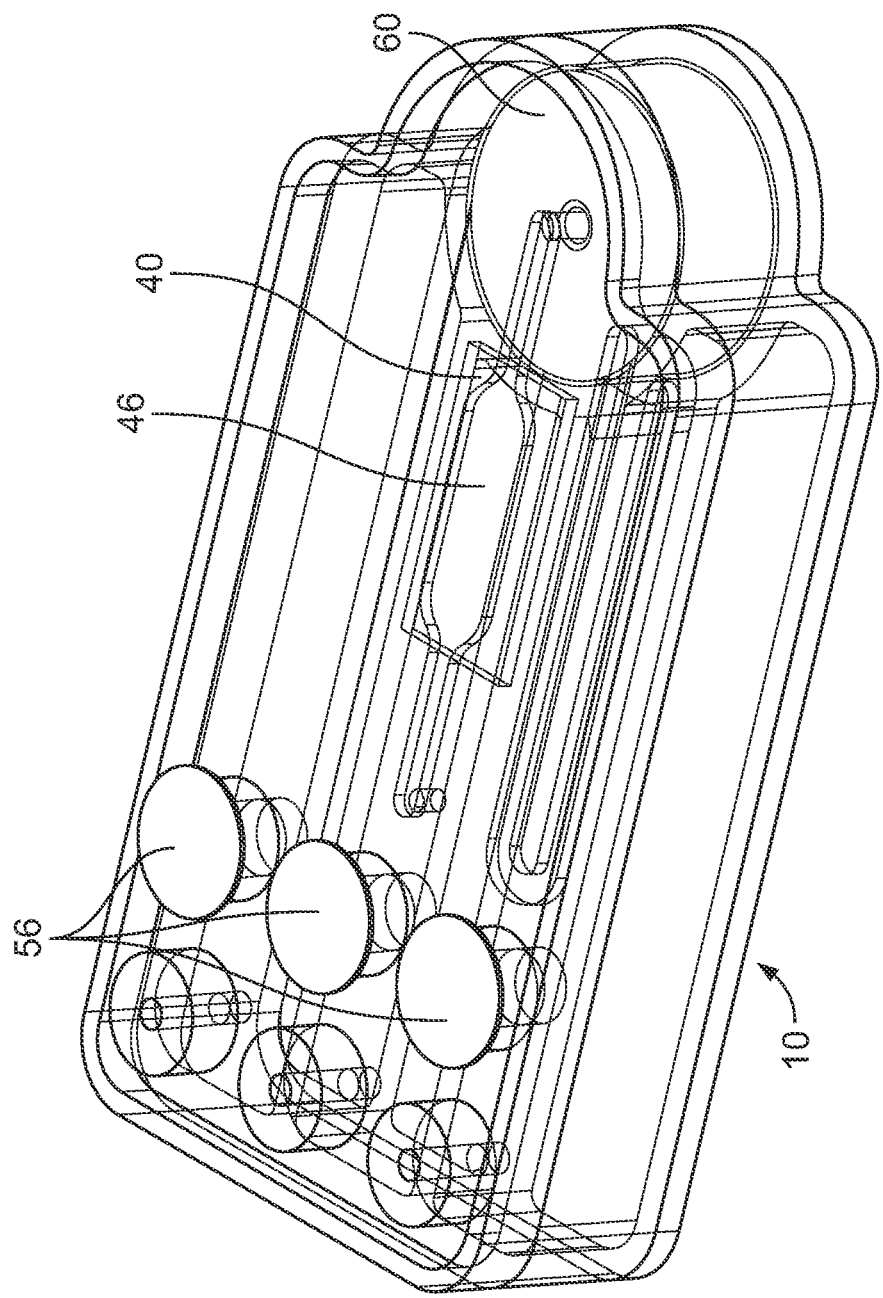
FIG. 3 is a further perspective view of the lab-on-a-chip cartridge of FIG. 1.

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Turning to the drawings, a lab-on-a-chip cartridge 10 is provided that comprises a housing 12 having a series separate chambers on the interior thereof. As best seen in FIGS. 7-10, the housing 12 comprises a top plate 14, a bottom plate 16, and an intermediate or middle plate 18 positioned between the top and bottom plates. The plates 14, 16, 18 of the housing 12 may be made by injection molding of a rigid medical grade plastic material. By way of example, the cartridge 10 may have an overall length of approximately 80 mm, a width of 40 mm and a thickness of 18.5 mm.

More specifically, the middle plate 18 has a top face 20 from which a plurality of side wall members 22 depend that define the various chambers of the cartridge 10, specifically, a whole blood chamber 24, a plasma chamber 26, a red blood cell (RBC) chamber 28 and a separation chamber 30. The top face 20 of the middle plate 18 is of a sufficient thickness so that a red blood cell concentrate (RCC) flow path 32 may be formed therein, the RCC flow path 32 including a first port 34 on one end in communication with the separation chamber 30 for flowing RCC into the flow path 32 and a second port 36 on the other end for flowing RCC into the RBC chamber 28. The top face 20 of the middle plate also includes a cut-out 38 for receiving the lab on a chip 40. The portion of the side walls 22 separating the whole blood chamber 24 from the separation chamber 30 includes a cut-out 42 to permit whole blood to flow from whole blood chamber 24 into the separation chamber 30. The bottom plate 16 is secured to the side wall members 22 to close the chambers and may include or define a pin 90 for alignment of a rotatable filter membrane 60 (which will be described in greater detail).

The top plate 14 has a bottom face 44 that, when the cartridge 10 is assembled, contacts the top face 20 of the middle plate 18. The bottom face 44 of the top plate 14 is of a sufficient thickness so that a plasma flow path 46 may be formed that is aligned with the lab-on-a-chip 40 mounted to the top face 20 of the middle plate 18, so that plasma may flow from the separation chamber 30 through a port 48 in the top face 20 of the middle plate 18, into the plasma flow path 46 where it contacts the lab-on-a-chip device 40, and then flow into the plasma chamber 26 through a port 50 in the top face 20 of the middle plate 18.

An input or injection port 52 is formed through the bottom face 44 of the top plate 14 and the top face 20 of the middle plate 18, through which whole blood may be injected into the whole blood chamber 24. Further, the bottom face 44 of the top plate 14 and the top face 20 of the middle plate 18 also include extraction ports 54a, 54b formed therein through which separated plasma (extraction port 54a) or red blood cells (extraction port 54b) may be withdrawn for additional testing, such as elution assays. An adhesive seal 56 preferably overlies each of the injection and extraction ports 52, 54a, 54b which may be lifted to provide access to the ports and then reseal the ports.

Each of the whole blood, plasma and red blood cell chambers 24, 26, 28 also has a pump interface 58 associated therewith through the bottom face 44 of the top plate 14 and the top face 20 of the middle plate 18. The pump interfaces 58 may each be in the form of a recessed well formed in the bottom face 44 of the top plate 14, with a flexible diaphragm (not shown) overlying each recessed well to seal the interface. Positive and negative pressure is applied to the diaphragms through a separate device (not shown), to direct fluid flow through the various chambers of the cartridge.

In keeping with the disclosure, a rotatable filter membrane 60 is disposed within the separation chamber 30, so that the cartridge 10 includes an integral spinning membrane separator for separating whole blood into plasma and red blood cell fractions. The use of spinning member separators is well established in the field of apheresis, where whole blood is withdrawn from a patient or donor or other blood source (which may include precollected blood in a container), separated into its constituents (e.g., plasma, red blood cells, white blood cells, and platelets), and one or more of the constituents reinfused into the patient or donor or other blood source. A spinning membrane separator is particularly well suited for extracting plasma from whole blood. Spinning membrane separators for apheresis are described in U.S. Pat. No. 5,194,145 to Schoendorfer and in U.S. Pat. No. 9,381,291 to Boggs et al., both of which are incorporated herein by reference, and which can be referenced for further details.

In general, a spinning membrane separator includes a generally cylindrical housing with an internal spinning member rotatably mounted therein, a gap being formed between the interior surface of the housing and the exterior surface of the spinner. As described in the above-referenced patents, the spinner comprises a central mandrel or rotor having a central orifice, to which a porous membrane is mounted. The outer surface of the rotor is typically shaped to define a series of spaced-apart circumferential grooves that are interconnected by longitudinal grooves so that matter passing through the porous membrane is able to flow into the interior of the spinner. When used for separating plasma from whole blood, the porous membrane typically has a nominal pore size of 0.6 µm. The housing includes an inlet through which whole blood is introduced into the gap, a first outlet in communication with the gap through which separated red blood cells are flowed, and a second outlet in communication with the interior of the spinner through which separated plasma is flowed.

Figure 5:
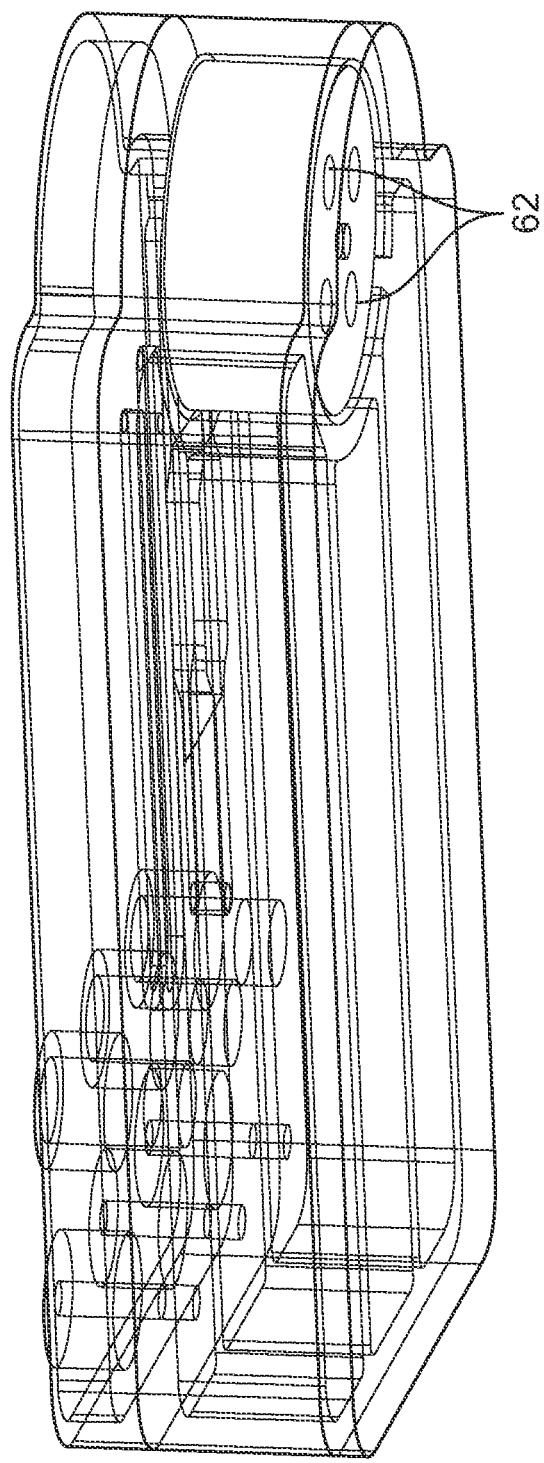
FIG. 5 is a further perspective view of the lab-on-a-chip cartridge of FIG. 1 showing the bottom face of the cartridge.
Figure 6B:
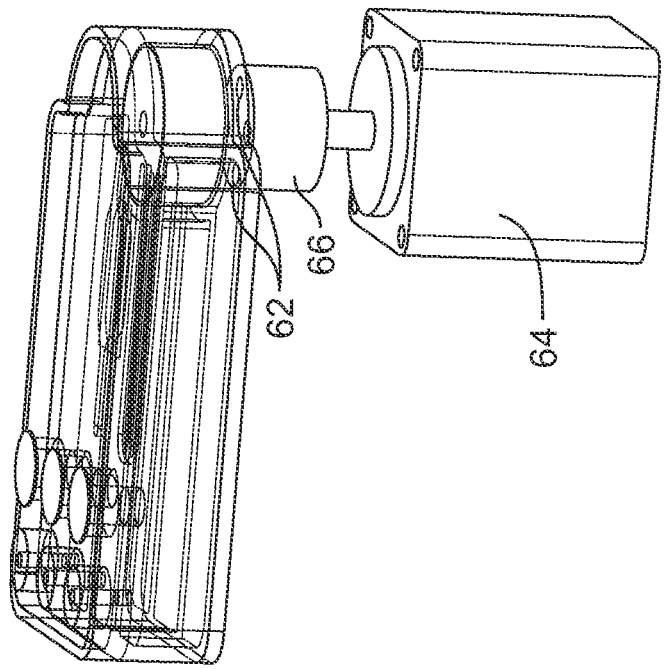
FIGS. 6A and 6B are perspective views of the lab-on-a-chip cartridge of FIG. 1 in combination with a separate drive mechanism for rotating the membrane of the separator.
Figure 6A:
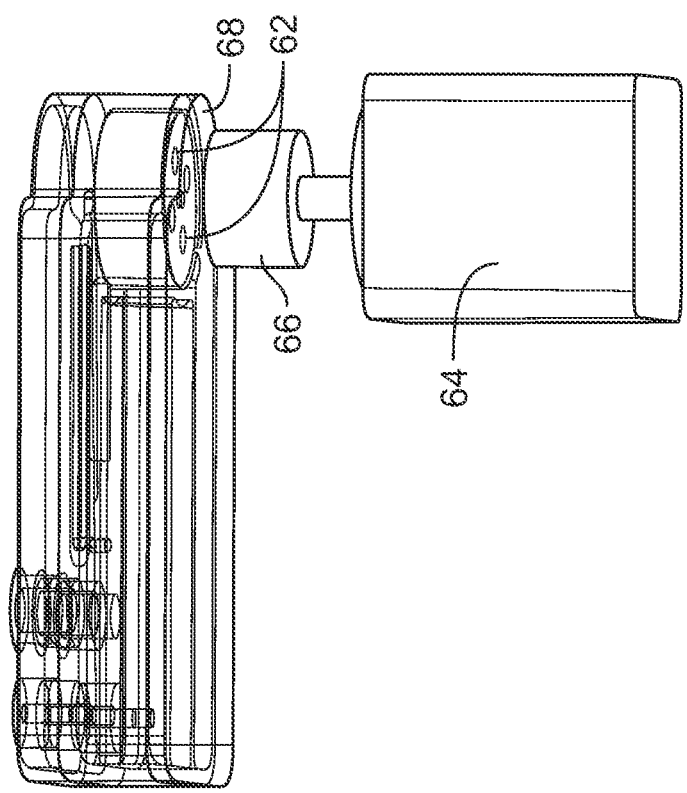
Figure 7B:
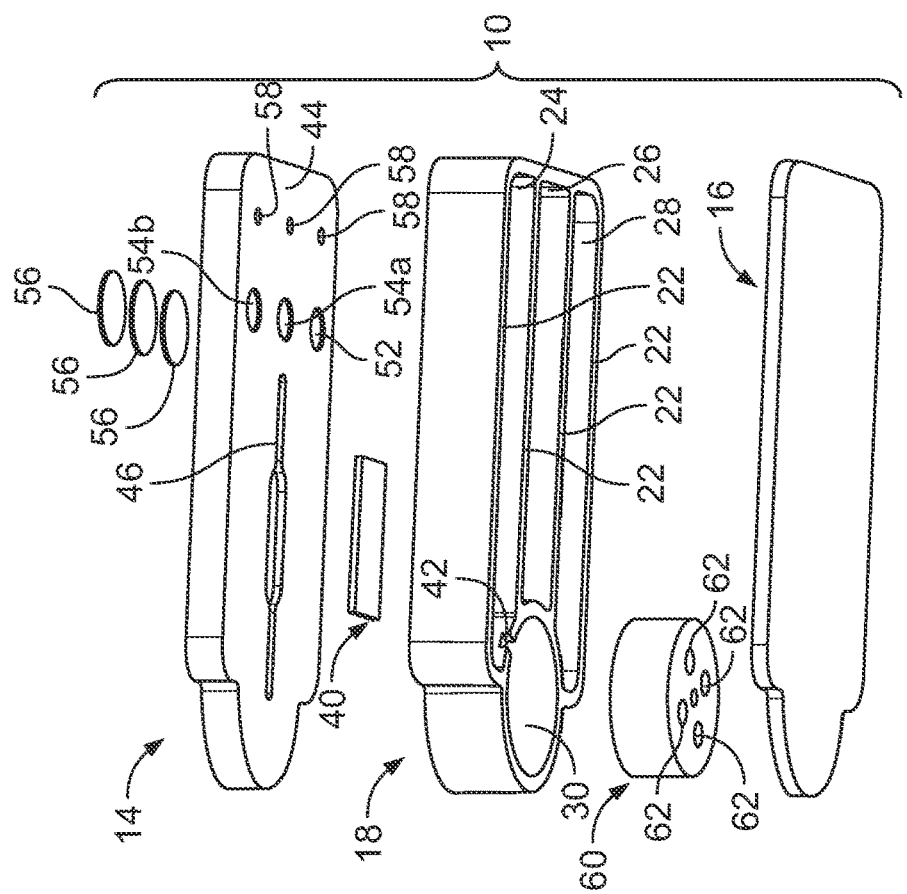
FIGS. 7A and 7B are exploded perspective views of the lab-on-a-chip cartridge of FIG. 1 showing the top surface and the bottom surface, respectively, of the subparts of the cartridge.
Figure 7A:
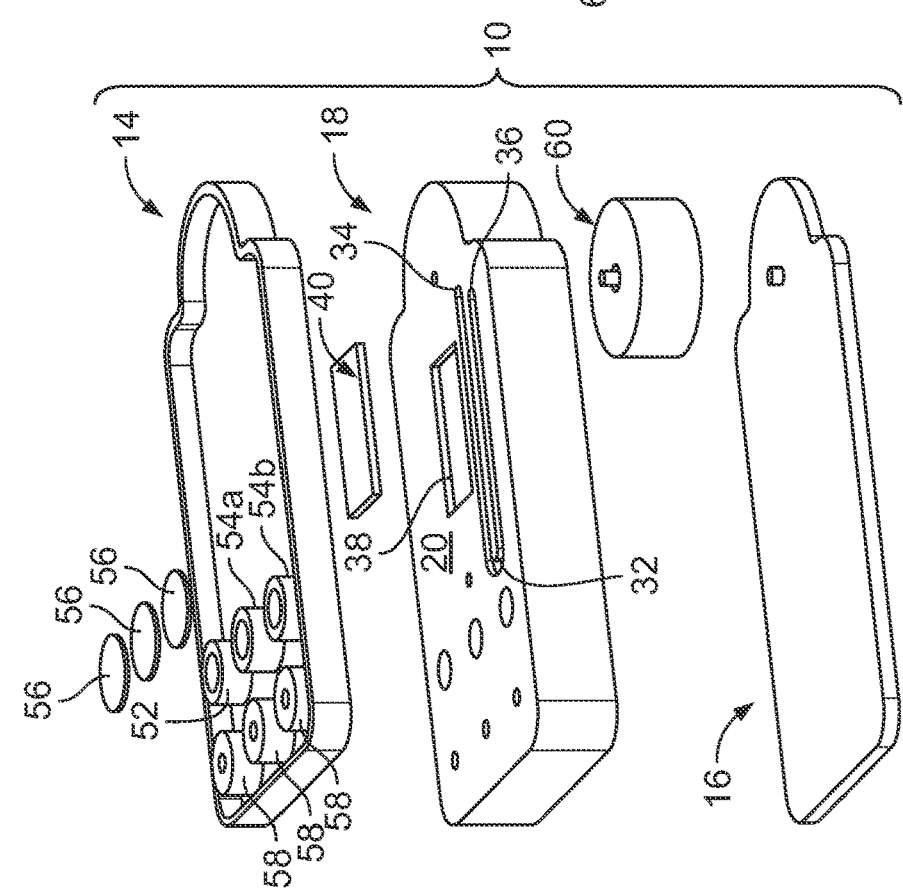
Figure 8B:
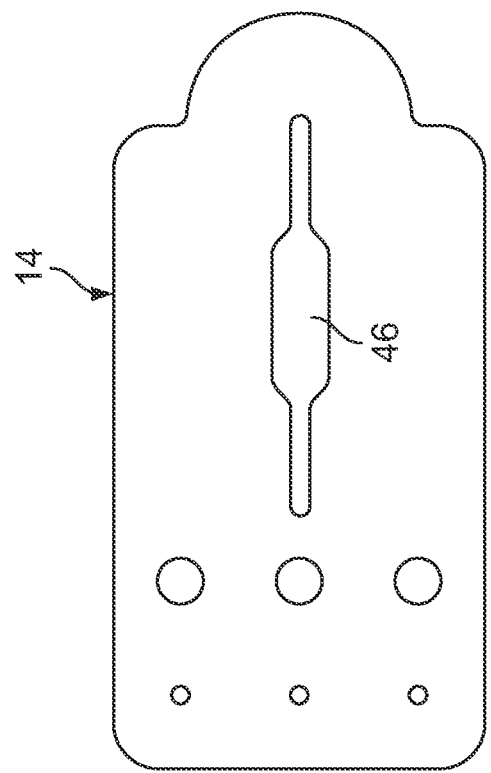
FIGS. 8A-8D are top and bottom views of the top plate of the lab-on-a-chip cartridge of FIG. 1.
Figure 8A:
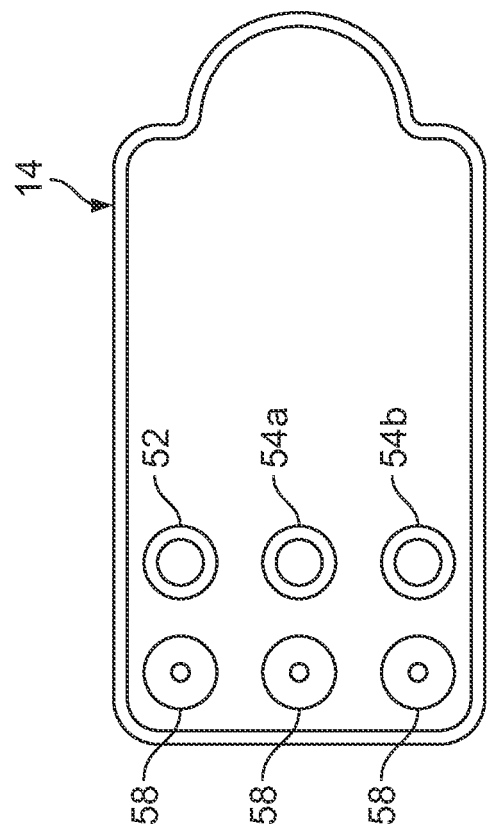
Figure 8D:
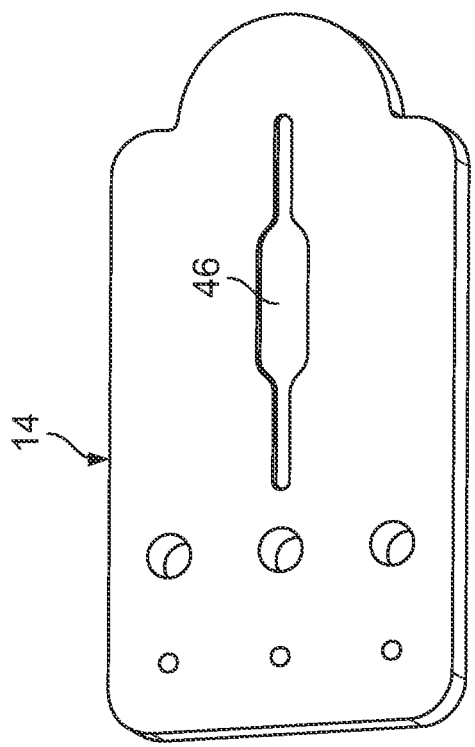
Figure 8C:
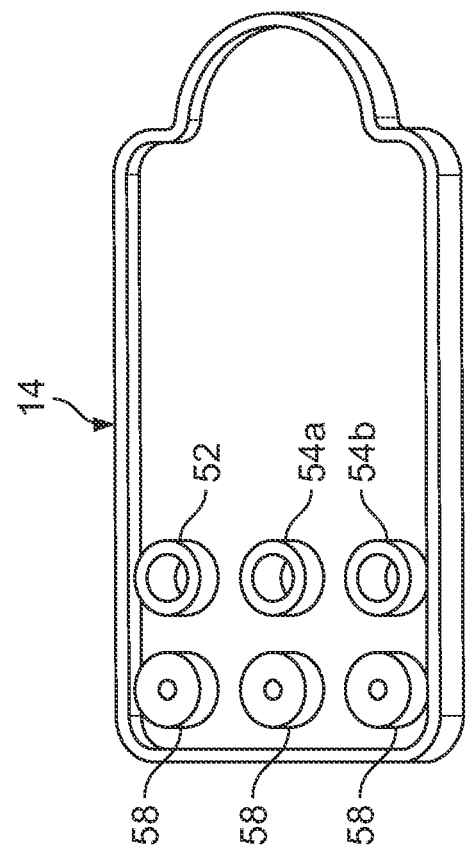
Figure 9B:
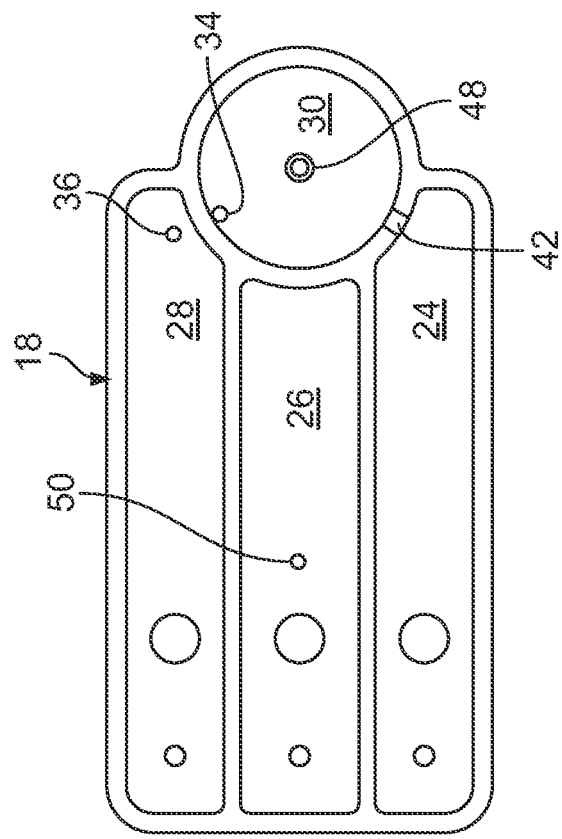
FIGS. 9A-9D are top and bottom views of the middle plate of the lab-on-a-chip cartridge of FIG. 1.
Figure 9A:
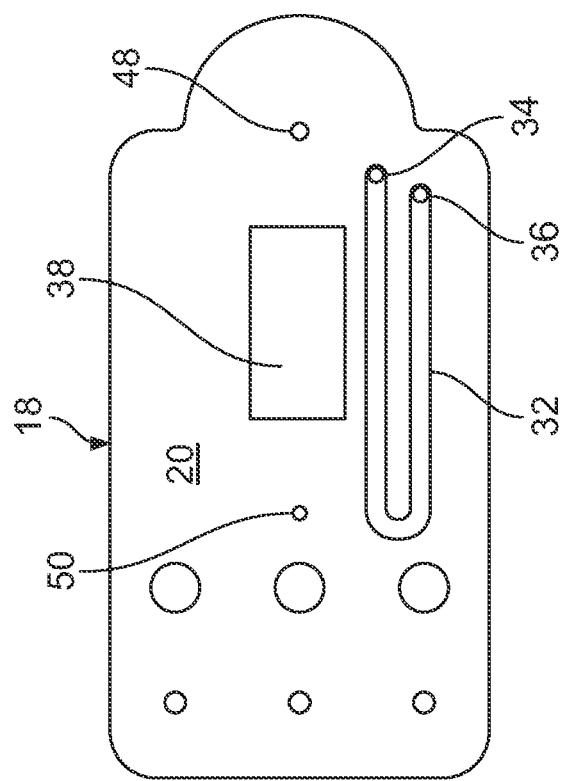
Figure 9D:
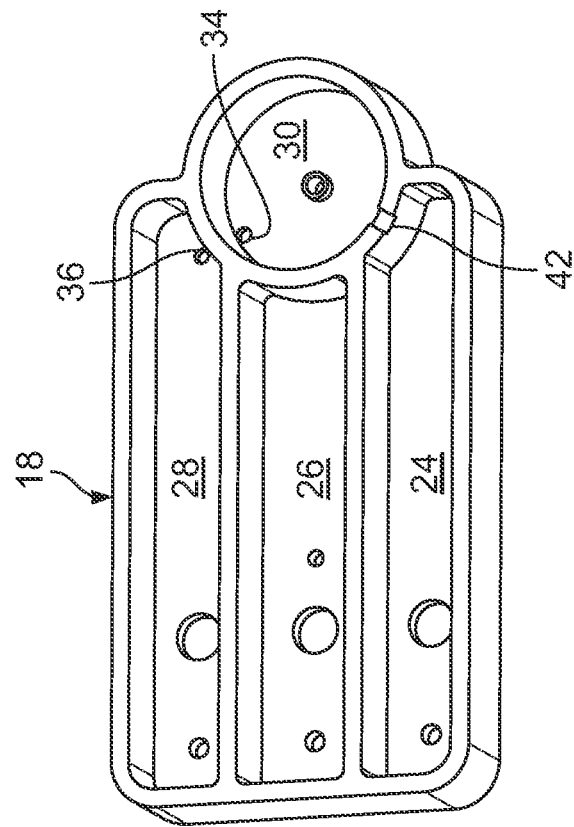
Figure 9C:
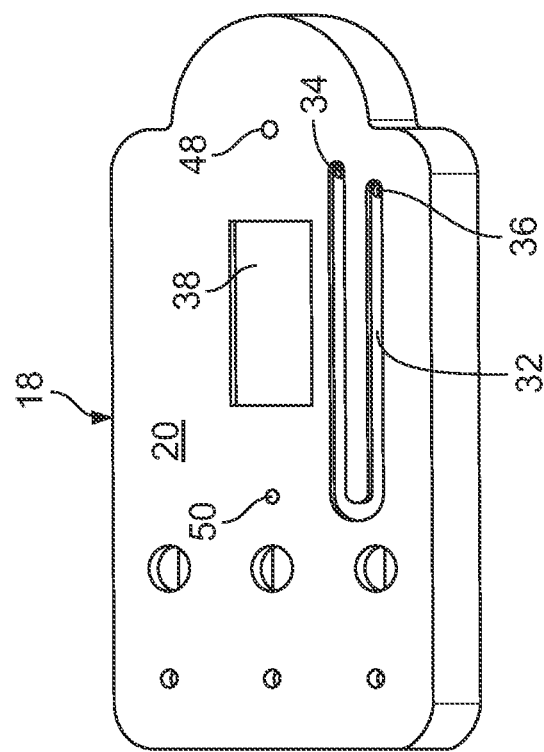
Figure 10A:
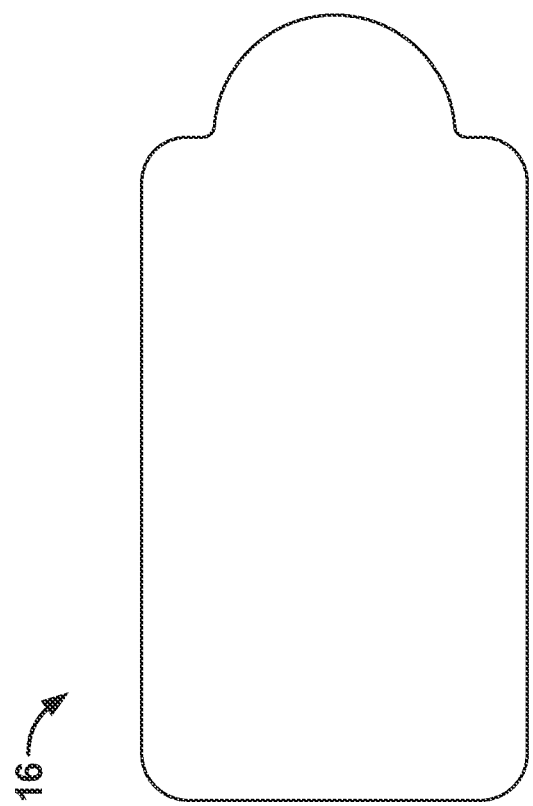
FIGS. 10A-10D are top and bottom views of the bottom plate of the lab-on-a-chip cartridge of FIG. 1.
Figure 10B:
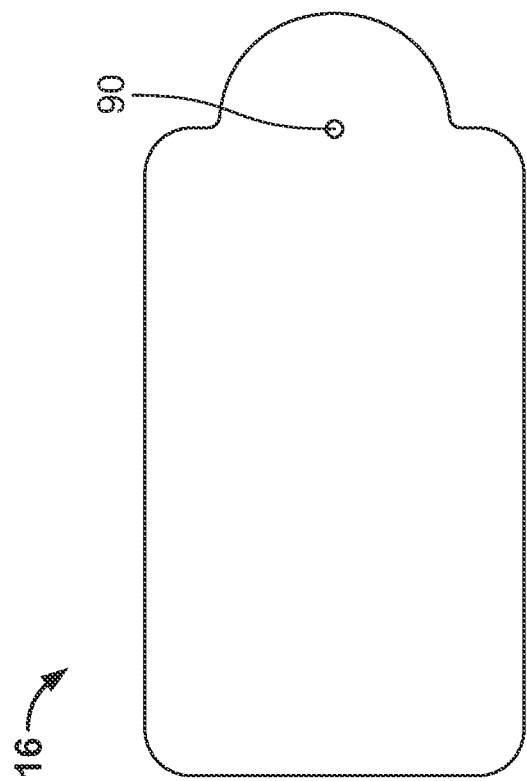
Figure 10D:
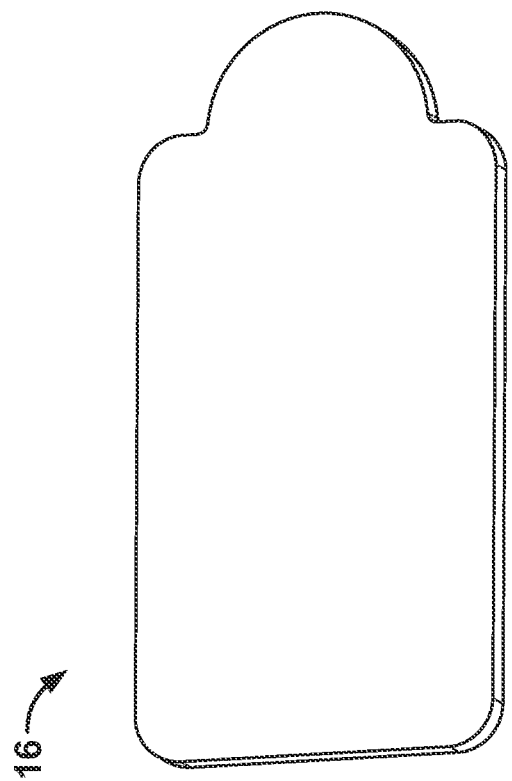
Figure 10C:
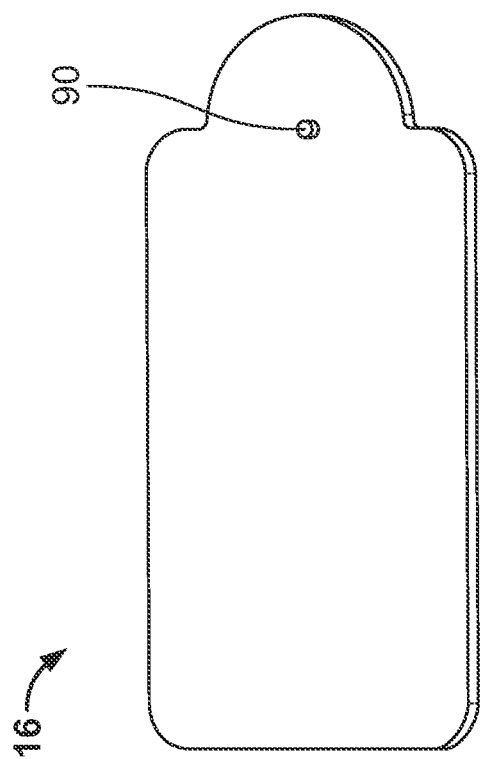
Figure 13:
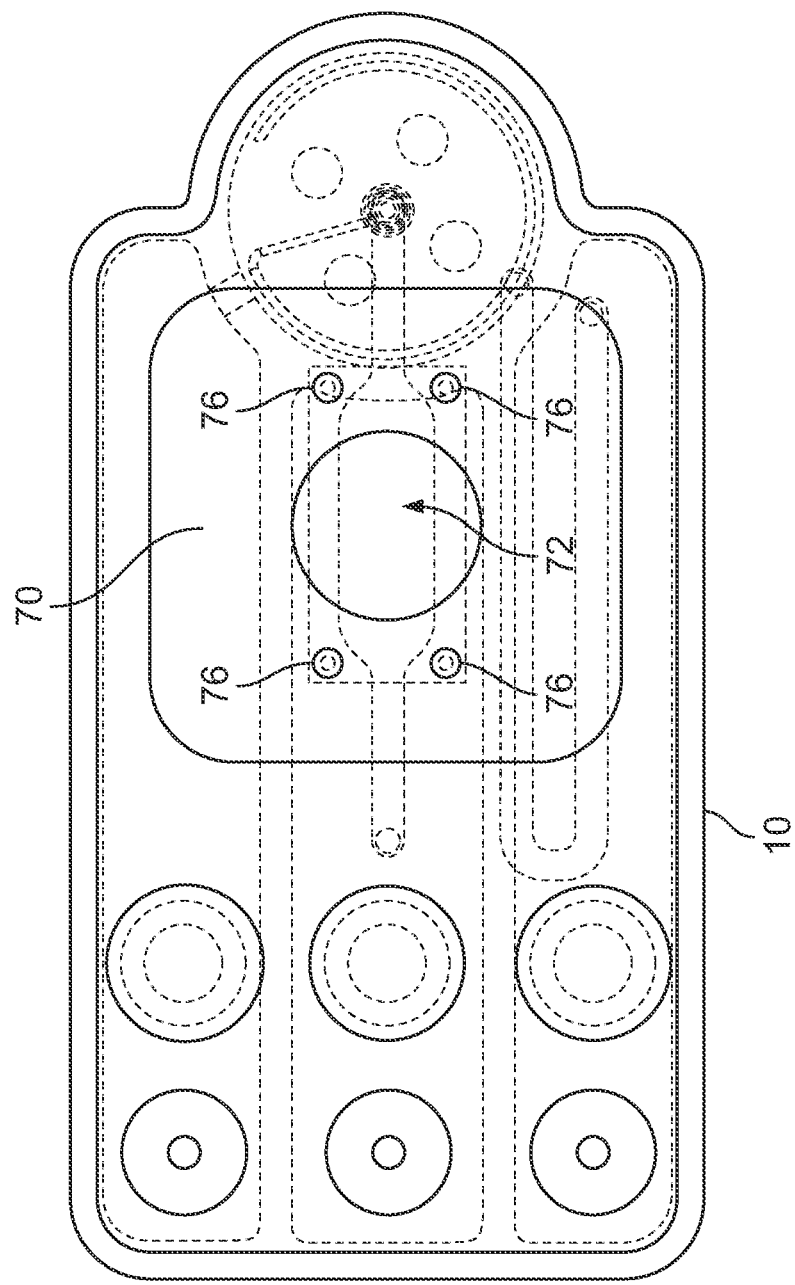
FIG. 13 is a top view of the top plate of the lab-on-a-chip cartridge in combination with the interface.

The spinner is typically rotated using a magnetic drive assembly, in which an end portion of the spinner is encompassed by as ring of permanent magnetic material 62 (as seen in FIGS. 5, 6a and 6b), so that a drive mechanism 64 having a magnetic drive member 66 external to the cartridge 10 is indirectly coupled to the rotatable filter membrane 60. As the drive member 66 is rotated, magnetic attraction between the drive member 66 and the rotatable filter membrane 60 locks the rotatable membrane 60 to the drive member 66, so that rotation of the drive member 66 rotates the membrane 60. To this end, one of the faces of the cartridge 10 (as shown, the lower face of the bottom plate 16) may be provided with an interface 68, such as a recessed area, for seating and aligning the drive member of the drive mechanism with the magnetic members 62 of the rotatable membrane 60.

Figure 4A:
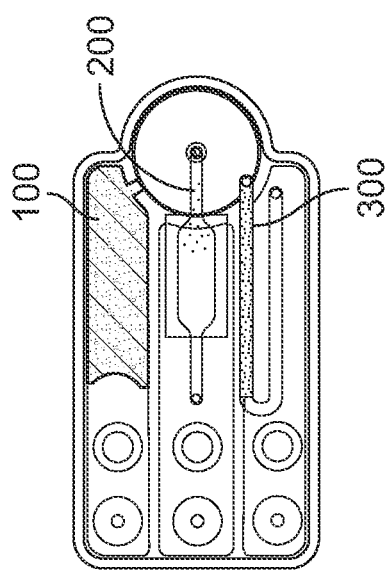
FIGS. 4A-4E are top views of the lab-on-a-chip cartridge of FIG. 1 showing the workflow through the cartridge.
Figure 4B:
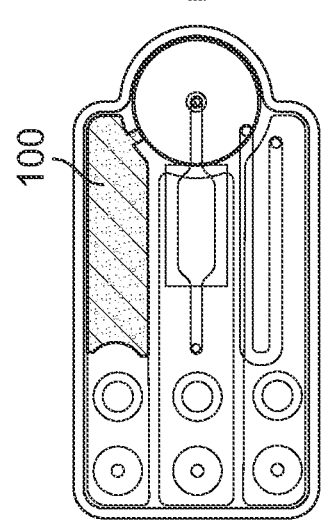
Figure 4C:
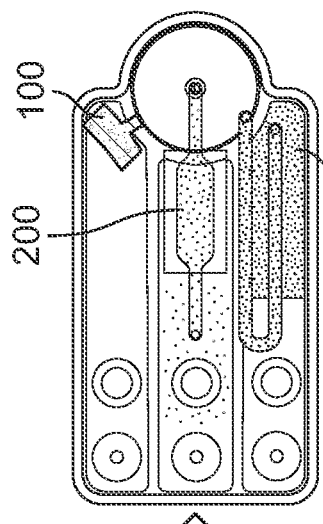
Figure 4D:
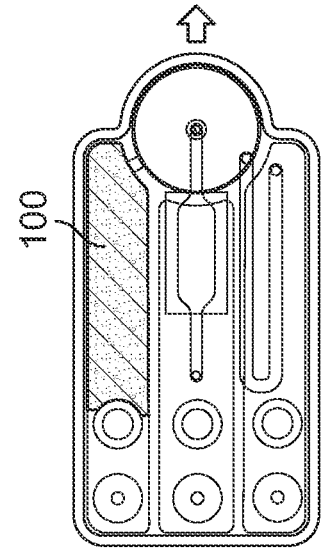
Figure 4E:
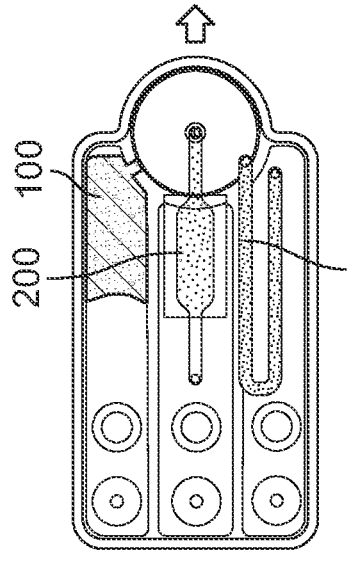

In use, a small volume of whole blood 100 is withdrawn from a patient and introduced into the whole blood chamber 24 of the cartridge through the injection port 52 by means of, e.g., a syringe (FIG. 4A). Then the whole blood 100 is pushed into the separation chamber 30 of the cartridge by action of a pump associated with pump interface 58 for the whole blood chamber 24 (FIG. 4B). The membrane 60 is rotated through magnetic coupling to an external drive device 64 to create Taylor vortices in the gap between the outer surface of the filter membrane and the inner wall of the separation chamber 30. Flow into and out of the separation chamber 30 is controlled by pumps associated with the various pump interfaces 58 so that plasma 200 (with biomarkers) is pushed through the membrane 60 and flowed out of the separation chamber 30 into the plasma flow path 46, where it contacts the lab-on-a-chip 40, while the red blood cells 300 (and other cellular material remaining in the gap) is flowed out of the separation chamber 30 into the red blood cell fluid flow path 32 (FIG. 4C). Whole blood 100 continues to be introduced into the separation chamber 30, separated into plasma and red blood cells, and plasma flowed into the plasma flow path 46 and red blood cells flowed into the red blood cell flow path 32 until the flow paths are filled (FIG. 4D), and then spill over into the plasma and red blood cell chambers (FIG. 4E).

In addition, the housing 12 of the cartridge 10 may be provided with one or more interfaces to provide for additional functionality. For example, an interface may be provided on the exterior of the housing for thermal regulation (e.g., cooling or thermal cycling) of the lab-on-a-chip device, to permit imaging of the surface of the lab-on-a-chip device, or to permit the application, control and sensing of electrical signals to and from the lab-on-a-chip device as plasma flows over the surface of the device.

With reference to FIGS. 11-14, an interface 70 in lens interface system 110 is shown that may provide for each of the functionalities described above. For example, the interface 70 may be associated with the top surface of the top plate 14 to provide for thermal-electric cooling of the plasma flow path 46 by conduction through the top plate 14. Additionally, or alternatively, the interface 70 may include a transparent material 72 to permit imaging of the chip by means of, e.g., a microscopic objective lens 74. Further, the interface may additionally or alternatively include conductive pins 76 that extend through the top surface of the top plate 14 to contact electrical pads 78 on the surface of the chip 40 to permit that transmission of electrical signals to and from the chip 40.

Thus, an LOC device having an integrated blood separator is provided that extracts plasma from a whole blood sample that is placed directly into a point-of-care device in which it can be analyzed. By way of the device, the need for a stand-alone centrifuge is eliminated, and larger sample volumes can be collected than current static membrane plasma separation devices allow, thus enabling low concentration biomarkers to be analyzed. As a result, plasma IVD could be performed at a hospital bedside or at remote locations outside a medical center for real-time health decision making for underserved populations.

It will be understood that the embodiments described above are illustrative of some of the applications of the principles of the present subject matter. Numerous modifications may be made by those skilled in the art without departing from the spirit and scope of the claimed subject matter, including combinations of features that are individually disclosed or claimed herein.

The invention claimed is:

1. A lab-on-a-chip cartridge comprising:
   a) a housing comprising a plurality of side wall members defining first, second, third and fourth separate chambers on the interior of the cartridge;
   b) each of the first, second and third chambers having a pump interface associated therewith;
   c) at least the first chamber having a port through which a fluid may be introduced into the first chamber;
   d) a filter membrane rotatably mounted in the fourth chamber so as to define a gap between an outer surface of the filter membrane and an inner surface of the side wall member defining the fourth chamber;
   e) a first passageway extending between the first chamber and the gap in the fourth chamber;
   f) a first flow path extending between the fourth chamber and the second chamber to permit fluid flow between an inner surface of the filter membrane and the second chamber, with a lab-on-a-chip device comprising an integrated circuit positioned within the first flow path and configured to contact fluid flowing into the second chamber;
   g) a second flow path extending between the fourth chamber and the third chamber to permit fluid flow between the gap in the fourth chamber and the third chamber; and h) an interface in an exterior surface of the fourth chamber configured to couple a drive device with the filter membrane for rotating the filter membrane.

2. The lab-on-a-chip cartridge of claim 1 wherein the housing further comprises a top plate, a bottom plate, and an intermediate plate between the top and bottom plates defining the side wall members, with the first flow path, second flow path, pump interfaces, port and drive device interface being contained within one of the top and bottom plates.

3. The lab-on-a-chip cartridge of claim 2 further comprising a second interface associated with the top plate to permit at least one or more of thermal regulation of the lab-on-a-chip device, imaging of a surface of the lab-on-a-chip device, and the application, control and sensing of electrical signals to and from the lab-on-a-chip device.

4. The lab-on-a-chip cartridge of claim 2, wherein the intermediate plate includes a cut-out configured to receive the lab-on-a-chip device.

5. The lab-on-a-chip cartridge of claim 1 wherein each of the pump interfaces comprises a recessed well sealed with a flexible diaphragm.

6. The lab-on-a-chip cartridge of claim 1 wherein the port includes an adhesive seal.

7. The lab-on-a-chip cartridge of claim 1 wherein the port is positioned between the pump interface of the first chamber and the first passageway.

8. The lab-on-a-chip cartridge of claim 1 wherein each of the second and third chambers includes a port through which a fluid may be extracted.

9. The lab-on-a-chip cartridge of claim 8 wherein each port includes an adhesive seal.

10. The lab-on-a-chip cartridge of claim 8 wherein the port of the second chamber is positioned between the pump interface of the second chamber and the first flow path.

11. The lab-on-a-chip cartridge of claim 8 wherein the port of the third chamber is positioned between the pump interface of the third chamber and the second flow path.

12. The lab-on-a-chip cartridge of claim 1 wherein the drive device interface comprises a recessed area.

13. The lab-on-a-chip cartridge of claim 1 wherein the first chamber is a whole blood chamber, the second chamber is a plasma chamber, the third chamber is a red blood cell chamber, the fourth chamber is a separation chamber, the first flow path is a plasma flow path, and the second flow path is a red blood cell flow path.

14. The lab-on-a-chip cartridge of claim 1 wherein the filter membrane includes magnetic material configured to couple the filter membrane to the drive device.

15. The lab-on-a-chip cartridge of claim 1 wherein the first, second, and third chambers are elongated and oriented substantially parallel to each other.

16. The lab-on-a-chip cartridge of claim 15 wherein:
the fourth chamber is substantially circular,
the second chamber is positioned between the first and third chambers, and
a portion of the fourth chamber is positioned between the first and third chambers.

17. The lab-on-a-chip cartridge of claim 1 wherein the first flow path is substantially linear.

18. The lab-on-a-chip cartridge of claim 1 wherein the first flow path has a non-uniform width, with a portion of the first flow path having a maximum width being at least partially aligned with the lab-on-a-chip device.

19. The lab-on-a-chip cartridge of claim 1 wherein the second flow path is generally U-shaped.

20. A method of extracting plasma from whole blood and analyzing it with a lab-on-a-chip cartridge comprising:
a. withdrawing whole blood from a blood source and introducing the whole blood into a first chamber of the lab-on-a-chip cartridge through an injection port;
b. pumping the whole blood into a separation chamber of the lab-on-a-chip cartridge with a filter membrane;
c. rotating the filter membrane and filtering the whole blood so that plasma passes through the filter membrane and flows out of the separation chamber and into a plasma flow path of the lab-on-a-chip cartridge where the plasma contacts a lab-on-a-chip device of the lab-on-a-chip cartridge, and red blood cells flow out of the separation chamber and into a red blood cell fluid flow path of the lab-on-a-chip cartridge; and
d. analyzing the plasma with the lab-on-a-chip device, wherein the lab-on-a-chip device comprises an integrated circuit.

* * * * *